United States Patent
Mundy et al.

(10) Patent No.: US 8,515,011 B2
(45) Date of Patent: Aug. 20, 2013

(54) SYSTEM AND METHOD FOR DOSE VERIFICATION RADIOTHERAPY

(75) Inventors: Daniel W. Mundy, Rochester, MN (US); Michael G. Herman, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 9 days.

(21) Appl. No.: 13/375,568

(22) PCT Filed: Jun. 2, 2010

(86) PCT No.: PCT/US2010/037067
§ 371 (c)(1),
(2), (4) Date: Feb. 24, 2012

(87) PCT Pub. No.: WO2010/141583
PCT Pub. Date: Dec. 9, 2010

(65) Prior Publication Data
US 2012/0140887 A1    Jun. 7, 2012

Related U.S. Application Data

(60) Provisional application No. 61/183,146, filed on Jun. 2, 2009.

(51) Int. Cl.
*A61N 5/10*    (2006.01)
*G01N 23/201*    (2006.01)

(52) U.S. Cl.
USPC .................. 378/65; 378/70; 378/86

(58) Field of Classification Search
USPC ............................. 378/6, 65, 70, 86
See application file for complete search history.

(56) References Cited

U.S. PATENT DOCUMENTS

| | | | | |
|---|---|---|---|---|
| 5,270,925 | A * | 12/1993 | Stegehuis | 378/7 |
| 5,317,616 | A * | 5/1994 | Swerdloff et al. | 378/65 |
| 5,528,650 | A * | 6/1996 | Swerdloff et al. | 378/65 |
| 5,696,806 | A * | 12/1997 | Grodzins et al. | 378/86 |
| 5,903,008 | A * | 5/1999 | Li | 250/363.04 |
| 5,905,809 | A * | 5/1999 | Timmer | 382/131 |
| 6,714,620 | B2 * | 3/2004 | Caflisch et al. | 378/65 |
| 7,471,813 | B2 * | 12/2008 | Ulmer et al. | 382/128 |
| 7,496,171 | B2 * | 2/2009 | Rinkel et al. | 378/7 |
| 7,573,039 | B2 * | 8/2009 | Smith | 250/370.09 |
| 7,623,625 | B2 * | 11/2009 | Boyden et al. | 378/86 |
| 8,107,589 | B2 * | 1/2012 | Sakurai et al. | 378/65 |
| 2002/0044628 | A1 | 4/2002 | Hussein et al. | |
| 2004/0017889 | A1 | 1/2004 | Kumakhov | |
| 2005/0023474 | A1 | 2/2005 | Persyk et al. | |
| 2006/0138332 | A1 | 6/2006 | Bryman | |
| 2008/0224061 | A1 | 9/2008 | Smith | |

OTHER PUBLICATIONS

International Search Report and Written Opinion under date of mailing of Jan. 14, 2010 in connection with PCT/US2010/037067.

* cited by examiner

*Primary Examiner* — Alexander H Taningco
(74) *Attorney, Agent, or Firm* — Quarles & Brady, LLP

(57) ABSTRACT

A system and method for performing dose verification during radiation therapy. The system images photons created by Compton scatter events in the patient receiving treatment using a Compton camera imager (CCI). A dose reconstruction method is provided to reconstruct acquired Compton scatter photon data to produce an image showing dose deposition in the subject.

22 Claims, 7 Drawing Sheets

SYSTEM AND METHOD FOR DOSE VERIFICATION RADIOTHERAPY

CROSS-REFERENCE TO RELATED APPLICATIONS

This application represents the national stage entry of PCT International Application No. PCT/US2010/037067 filed Jun. 2, 2010 which claims the benefit of U.S. Provisional Patent Application 61/183,146, filed Jun. 2, 2009, and entitled "SYSTEM AND METHOD FOR DOSE VERIFICATION IN RADIOTHERAPY," both of which are hereby incorporated herein by reference for all purposes.

BACKGROUND OF THE INVENTION

The field of the invention is radiotherapy and, in particular, the invention relates to a system and method for accurately performing dose verification for subjects receiving radiation therapy.

External beam radiation therapy is designed to selectively destroy tumor tissue by administering large, spatially-controlled doses of radiation to a subject. The "Rule of Thumb" for such procedures is that the dose delivered should be within ±5 percent of the planned dose and within ±5 mm of the planned position. The treatment process proceeds through a number of steps, beginning with a contoured dose prescription indicated by a radiation oncologist using a set of diagnostic images. A dosimetrist, with the aid of a treatment planning system (TPS), then determines the dose to be delivered from each of a set of beam geometries and incident angles. The TPS utilizes stored dosimetric information, which is typically obtained from measurements on phantoms, to deterministically calculate dose delivery. Once the treatment plan has been approved by the oncologist, the treatment regiment begins. Prior to radiation delivery, the subject is positioned as exactly as possible to match the position used for treatment planning. This includes the alignment of skin markers with room lasers and the acquisition of CT or x-ray images for registration with planning images using either intrinsic or extrinsic fiducial markers. Typically, kilovoltage imaging is performed using an on-board imaging device (OBI) or megavoltage imaging is performed using an electronic portal imaging device (EPID). Immobilization devices can also be used to further increase positioning accuracy and minimize movement during treatment. After proper measures are taken to ensure a subject accurately receives the planned treatment, the radiation dose is delivered, typically at a rate of approximately 400 to 600 cGy per minute.

In radiotherapy, a number of surrogates for determining actual dose delivery are used, some of which are implemented prior to treatment, some during, and some after. Specifically, careful planning and equipment quality assurance provide the basis for determining whether the dose that will be delivered is within ±5 percent of the planned dose and within ±5 mm of the planned position. For example, in one method for performing dose verification, the completed treatment plan can be applied to a tissue or water phantom and the dose may be measured inside the phantom using ion chambers or film. These measurements are then compared with point measurements in the treatment plan to ensure accuracy. Alternatively, EPID images acquired during the phantom irradiation can be compared with digitally reconstructed radiographs (DRRs) generated by the TPS.

Another method for performing dose verification includes placing diodes on the subject's skin to measure skin dose during treatment. Similarly, fiducial markers containing thermoluminescent dosimeters (TLDs) may be implanted in the tumor to measure dose at a number of points. More recently, an implantable MOSFET detector capable of transmitting absorbed dose data to an external handheld reader has been developed, though currently this technology is not widely employed. While skin diodes are non-invasive and provide instantaneous readings, the implanted devices require at least one invasive procedure and can be read only after dose has been delivered. The use of such devices generally adds another step to treatment preparation and reduces treatment efficiency.

Some work has been done to attempt to determine the delivered dose via EPID images obtained during treatment. Such approaches focus on reconstructing the photon fluence at the point of entry by correcting the fluence measured at the EPID for subject attenuation. The calculated entrance fluence is then used in a dose calculation algorithm, which is essentially another TPS, to "reconstruct" an estimate of the dose delivered to the subject.

All of these methods for performing dose verification suffer from the fact that they rely on indirect measurements for dose delivery once dose delivery is substantially occurred and they, accordingly, include inaccuracies associated with the indirect measurements or the ability to correlate actual dose delivery from the indirect measurement. Also, none of these dose verification methods provides three-dimensional measurements of delivered dose.

It would therefore be desirable to have a system and method for accurately quantifying the three-dimensional distribution of radiation dose in subjects receiving radiation therapy.

SUMMARY OF THE INVENTION

The present invention overcomes the aforementioned drawbacks by providing a system and method for directly measuring dose deposition in a subject receiving radiotherapy. A system is provided that includes a Compton camera imager (CCI) configured to detect photons that have been ejected from the subject due to Compton scattering induced by the radiation treatment. Acquired information describing the Compton scattered photons is then reconstructed to produce an image showing dose deposition in the subject.

In accordance with one aspect of the invention, a method for determining a dose of radiation delivered to a subject receiving radiotherapy is disclosed that includes acquiring photons resulting from Compton scatter in the subject using a Compton camera imager to produce a set of acquired Compton photon data. The method also includes backprojecting the acquired Compton photon data from the Compton camera imager to image space, deconvolving the backprojected Compton photon data, and reconstructing an image of the dose delivered to the subject from the deconvolved, backprojected Compton photon data.

In accordance with another aspect of the present invention, a system for performing a radiotherapy process includes a patient support configured to receive a subject of a radiotherapy process and a radiation source configured to deliver radiation to the subject in accordance with the radiotherapy process. The system also includes a first Compton camera imager configured to receive a first set of Compton photon data corresponding to Compton scatter in the subject at least due to the radiotherapy process and a second Compton camera imager configured to receive a second set of Compton photon data corresponding to Compton scatter in the subject at least due to the radiotherapy process. In addition, the system includes a processor connected to receive at least the first and second set of Compton photon data and configured to reconstruct an image of a dose delivered to the subject using the first and second set of Compton photon data, wherein an intensity of each voxel in the image of the dose delivered to the subject is substantially proportional to a number of source photon interactions at a corresponding location in the subject during the radiotherapy process.

Various other features of the present invention will be made apparent from the following detailed description and the drawings.

DETAILED DESCRIPTION OF THE INVENTION

The present invention provides a system and method for radiation dose verification that creates a three-dimensional image of energy deposited in a patient during radiotherapy treatments. The system utilizes Compton camera imagers to detect photons generated by a linear accelerator that scatter out of the patient after depositing some fraction of the initial energy, that is, after delivering a dose to the patient. The recorded detector events are back-projected to obtain a 3D image of relative energy deposition due to photon interactions. Comparison of the reconstructed image with the planned dose distribution provides direct, independent, in vivo verification of delivered dose, thereby ensuring that radiotherapy patients are treated in accordance with the prescribed treatment plan.

Figure 1A:
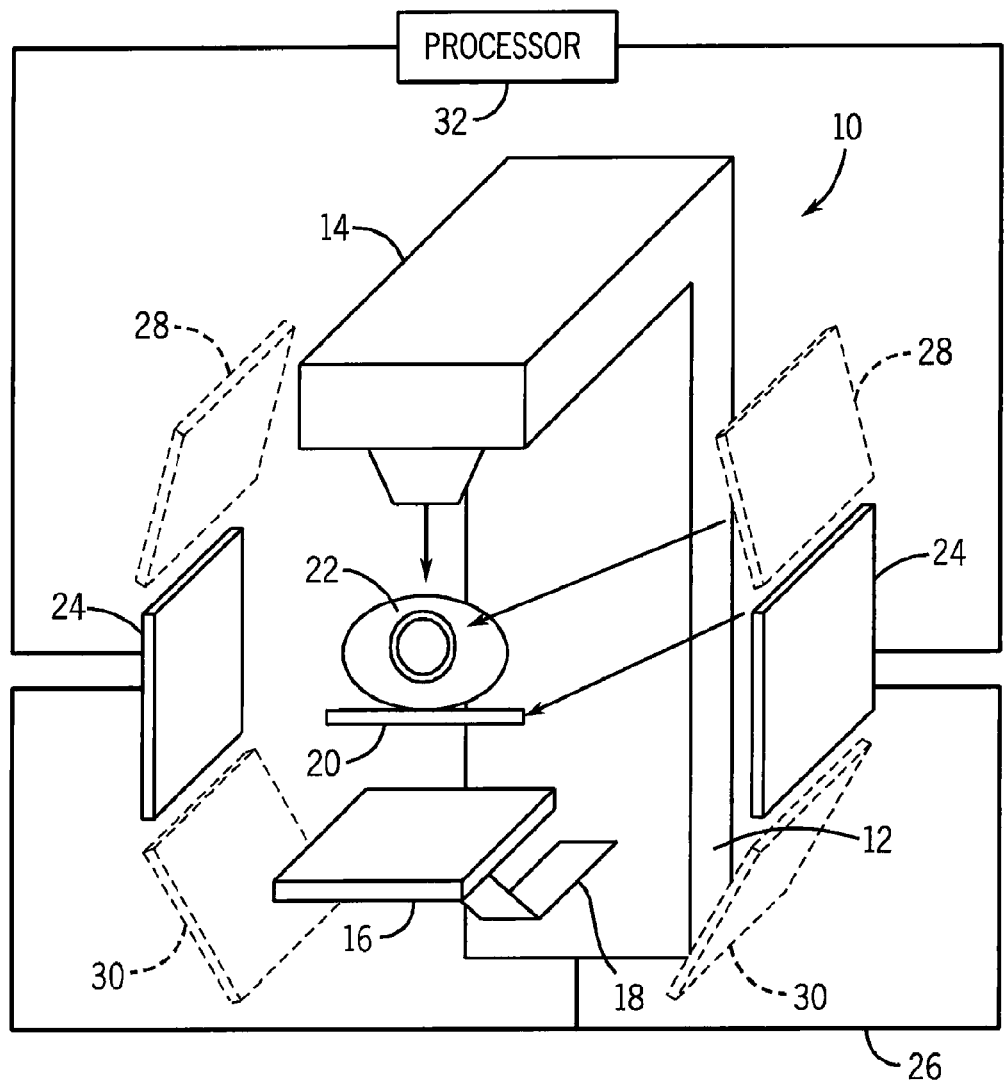
FIG. 1a is a schematic depiction of a radiotherapy system with dose verification using Compton camera imagers (CCI) in accordance with the present invention.

Referring to FIG. 1a, a radiation therapy system 10 in accordance with the present invention is illustrated. The radiation therapy system 10 is designed to perform traditional radiotherapy and, also, dose verification. To this end, the radiation therapy system 10 includes a base 12 having a LINAC 14 supported by the base 12 and disposed above an EPID 16, which may be attached to the base 12 via a movable arm 18. A treatment table 20 onto which a subject 22 (or phantom) may be placed is disposed between the LINAC 14 and the EPID 16. The radiation therapy system 10 further includes a Compton camera imager 24 configured to detect Compton scatter events. It is contemplated that a pair of such Compton camera imagers 24 may be attached to the base 12 via movable arms 26 so that the Compton camera imagers 24 can be positioned on opposing sides of the treatment table 20. Though FIG. 1a is illustrated as including two Compton camera imagers 24, it is recognized that, for at least some clinical applications, it may be suitable to reconstruct a desirable image using a single CCI system. Thus, it is contemplated that the following descriptions may be applicable to systems including only one CCI system.

Since the energy of a Compton scattered photon is dependent on the scattering angle, photons scattered at larger angles have lower energies. The movable arms 26 may therefore be configured to position the Compton camera imagers 24 in an upper octant, as depicted at 28, to increase exposure to low-energy photons. Likewise, the Compton camera imagers 24 may be placed in a lower octant, as depicted at 30, to increase exposure to high-energy photons. In any case, the Compton camera imagers 24 are connected to deliver acquired data sets to a processor 32 that, as will be described, is configured to reconstruct an image indicating a radiation dose received by the subject 22 during a radiotherapy process.

The components of the radiation therapy system 10 with dose verification may be selected and configured based on simulated system parameters determined using the Monte-Carlo model, as will be described below. For example, there are many possible designs and geometric configurations for the Compton camera imagers 24. The majority of available Compton camera designs fall into three main categories: parallel detectors, ring detectors, and stacked detectors. In choosing a Compton camera for the radiation therapy system 10, the choice of detector configuration is generally based on imaging performance and the physical size. Imaging performance is a function of many factors, including spatial resolution, energy-deposition resolution, and efficiency. Unfortunately, these properties may run contrary to one another. For example, the spatial resolution of a parallel detector configuration suffers from a PSF that is stretched in the dimension perpendicular to the detector plane. This is a result of low-angle detector events that produce nearly-overlapping reconstruction cones. A ring detector configuration excludes these low-angle events and increases spatial resolution, but at a high cost to efficiency, as the total number of photons available for image reconstruction is limited by the solid angle of the detector, relatively short treatment times, the scattering efficiency of the scatter detector, the absorption efficiency of the absorption detector, and the timing of the coincidence circuit. If the efficiency of the system is too low, then SNR suffers and a high spatial resolution may no longer be advantageous. The physical size of the imaging system is important when considering radiotherapy treatment room having limited space and the size of the reconstructed volume.

Figure 1B:
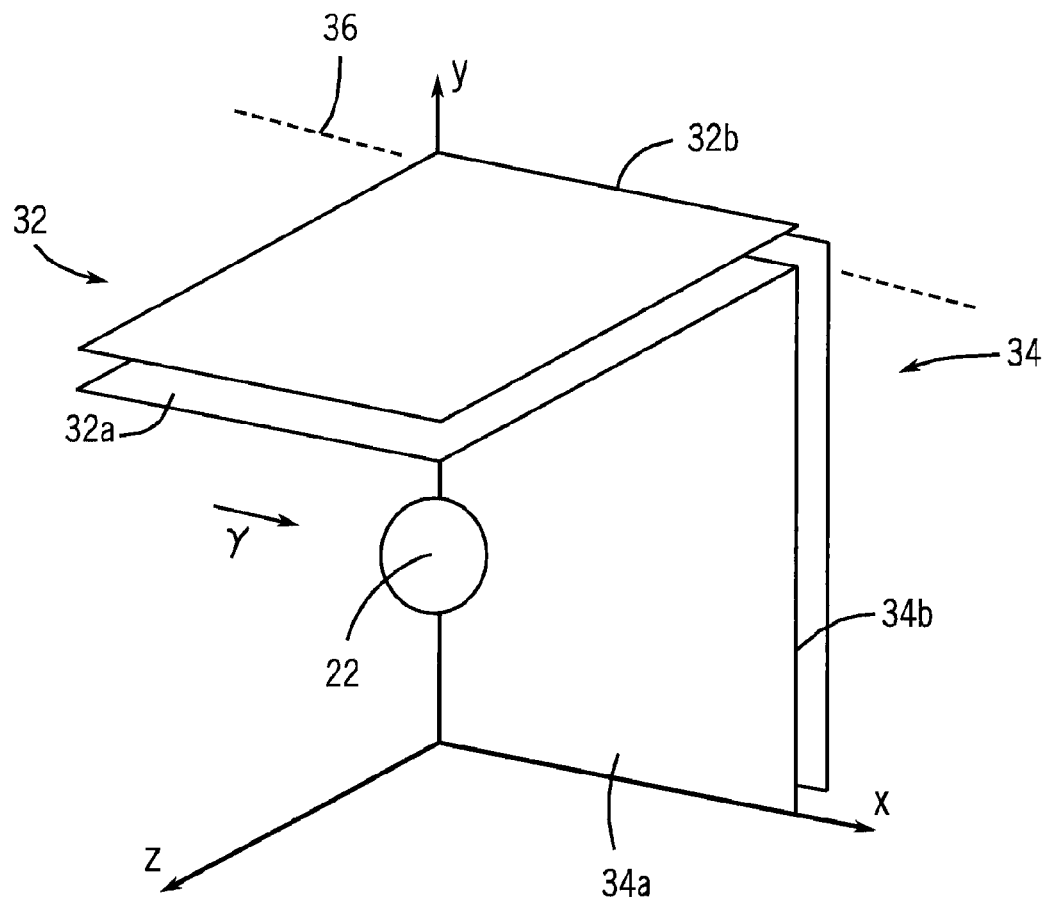
FIG. 1b is a schematic depiction of a CCI system for use with the radiotherapy system of claim 1a having two CCI sub-systems positioned along an adjacent edge.

Referring to FIG. 1b, a system including a single CCI system or system including two parallel opposed CCI systems, such as illustrated in FIG. 1a, cannot generally provide adequate resolution of an imaged object in the dimension perpendicular to the detector surfaces; Hence, FIG. 1b is a schematic illustration of a CCI sub-system for use with the radiotherapy system of FIG. 1a having two CCI sub-systems 32, 34 positioned to share a common, adjacent axis 36, such that the CCI sub-systems are arranged at an angle of approximately 90 degrees with respect to one another. This detector configuration provides an enhanced viewing angle, such that a sufficient 3D resolution can be attained in an economically practical manner and with reduced manufacturing complexity. Specifically, the CCI sub-systems 32, 34 may be mounted to the detection system on the linear accelerator gantry 14, of FIG. 1, or otherwise near the patient 22. While a larger number of detectors would theoretically provide better increased resolution, the expense and complexity of a feasible implementation makes the configuration illustrated in FIG. 1*b* advantageous.

As illustrated in FIG. 1*b* (and likewise applicable to the design illustrated in FIG. 1*a*), each of the CCI sub-systems 32, 34 includes a scatter detector 32*a*, 34*a* and an absorption detector 32*b*, 34*b*. As illustrated, an incident photon undergoes a Compton scattering event in the first, scatter detector 32*a*, 34*a*, after which it is absorbed in the second, absorption detector 32*b*, 34*b*. The measured energy deposition in the scatter detector 32*a*, 34*a* relative to the total photon energy (calculated as the sum of energies deposited in each detector) is used to calculate the angle through which the photon scattered in the first, scatter detector 32*a*, 34*a*. This angle, combined with the axis defined by the interaction positions in each detector 32, 34, defines a conical surface representing all possible points of origin of the detected photon. Considering an imaged point photon source, the overlap of the cone surfaces associated with multiple detector events indicates the physical position of the source in a 3D coordinate system. In this application, the photon source is comprised of photons scattered out of the patient during radiotherapy administration.

Figure 2:
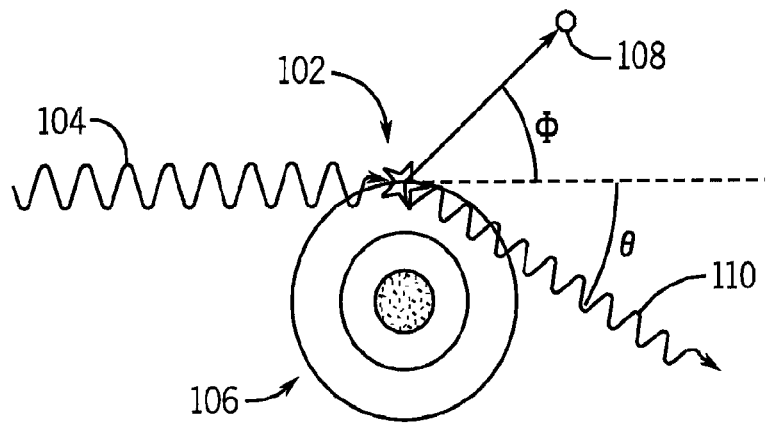
FIG. 2 is depiction of a Compton scatter event.

Specifically, referring to FIG. 2, in radiation therapy procedures, energy is transferred from a photon beam to a subject primarily via Compton collisions of the photons with electrons. Photoelectric and pair production interactions also occur, but to a lesser degree. In a Compton scatter event 102, an incident photon 104 strikes the electron cloud of a target atom 106 and generates a Compton electron 108 through which dose is transmitted and a Compton scattered photon 110. A rough calculation indicates that approximately $10^8$ or more Compton scattered photons per gram are generated every second during treatment, depending on photon energy.

Figure 3A:
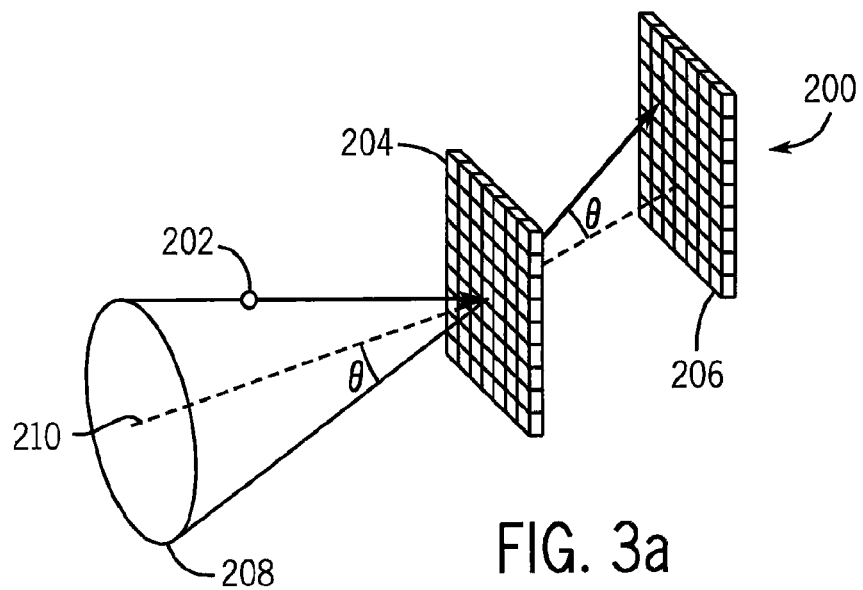
FIG. 3a is a schematic depiction of a Compton camera imager in accordance with the present invention.

Referring to FIG. 3*a*, Compton scattered photons may be measured using a CCI 200, or "Compton camera." As described above, these devices include one or more radiation detectors that utilize the Compton scattering process to ascertain the original point of origin of a detected gamma-ray, that is, photon. As also addressed above, CCI devices can have a variety of detector layouts, for example, parallel detectors, ring detectors, and multiple-Compton, or "stacked," detectors.

Figure 3B:
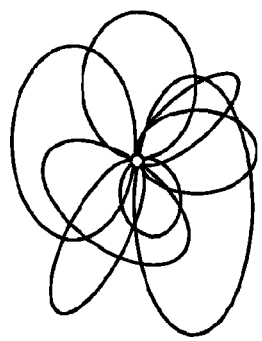
FIG. 3b is a schematic depiction of the back-projection of scatter cones in accordance with the present invention.

CCI systems typically operate on the principles illustrated in FIG. 3*a*. Specifically, a photon 202 emitted from a radiation source of interest (not shown) undergoes Compton scattering in a front "scatter" detector 204, which records the position of interaction and the fraction of initial photon energy transferred to the Compton electron. The scattered photon 202 then enters a second "absorption" detector 206, where it is completely absorbed via one or more Compton scatter or photoelectric interactions. The energy of the initial photon 202 is thus calculated as the sum of energies deposited in each of the detectors 204, 206. Compton scatter equations relating the energies of the incident and scattered photons to the angle of scattering can therefore be derived from conservation of energy and momentum as follows:

$$hv = hv' + E_{e^-}$$ Eqn. 1

$$hv' = \frac{hv}{1 + \alpha(1 - \cos\theta)}; \alpha = \frac{hv}{m_0 c^2};$$

where hv is the incident photon energy, hv' is the scattered photon energy, $E_{e^-}$ os the Compton electron kinetic energy, θ is the photon scattering angle, and $m_o c^2$ is the electron's rest mass. The angle θ specifies the half-angle of a cone 208 having an apex at the point of interaction in the scatter detector 204 and axis 210 along the line connecting the interaction points in both detectors 204, 206. This cone 208 surface represents the set of all possible source points of the incident photon 202. Referring to FIGS. 3*a* and 3*b*, if a point source 212 is placed in front the detectors 204, 206, the cone 208 surfaces constructed for multiple detector events will intersect at the location of the point source 212, as indicated in FIG. 3*b*. CCI systems 200 reconstruct the cone surfaces of many detector events in an image matrix to determine the physical locations of imaged photon sources.

This reconstruction method is prone to two sources of uncertainty. First, the axis of the cone 208 is determined by the points of interaction in the scatter and absorption detectors 204, 206 and is therefore dependent on the spatial resolution of the detectors. Second, the angle of the cone 208 is calculated from the Compton scatter equation and is, therefore, dependent on the energy of the Compton electron collected in the scatter detector and the scattered photon absorbed by the absorption detector. Thus, the position resolution of the system 200 has a dependence on the energy resolution of each detector. Dose uncertainty in a subject also has a dependence on system properties. Accordingly, the present invention provides a model for calculating the position and dose uncertainties of a CCI system as a function of the system parameters.

Figure 4:
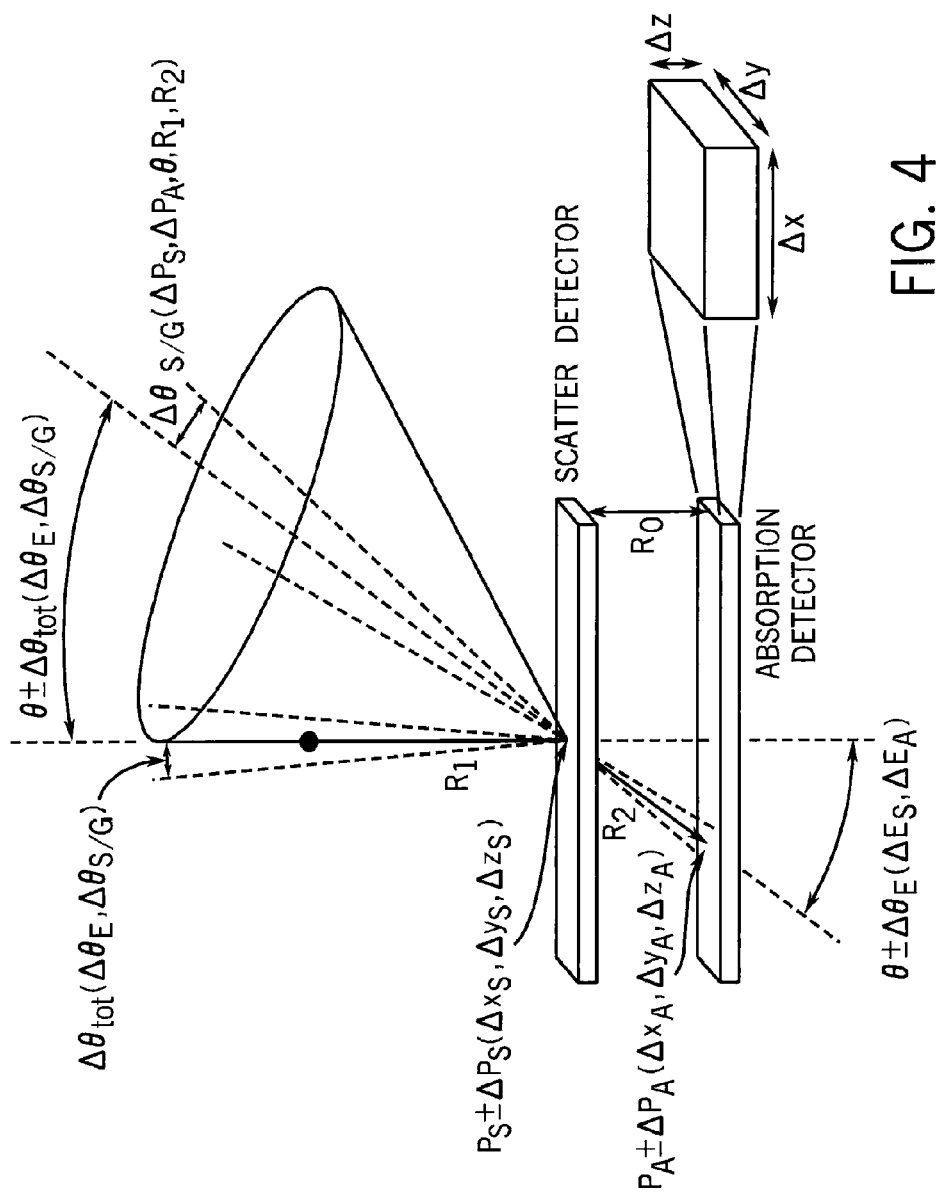
FIG. 4 is a schematic depiction of a Compton camera imager relating angular uncertainties to system parameters and geometry in accordance with the present invention.

Referring to FIG. 4, there are three primary contributors to angular uncertainty in a Compton camera system: detector energy resolution, detector spatial resolution, and system geometry. These factors determine the accuracy with which the apex, axis, and angle of the reconstruction cone can be calculated. FIG. 4 illustrates the complicated relationship between system parameters and the total angular uncertainty of the system. The total angular uncertainty $\Delta\theta_{tot}$ is dependent on two other independently-calculated angular uncertainties; that is, angular uncertainty due to detector energy resolutions $\Delta\theta_E$ and uncertainty due to detector spatial resolutions and system geometry $\Delta\theta_{S/G}$. The accuracy with which the scattering angle of a photon in the scatter detector θ is computed is dependent on detector energy resolution and this angle can be calculated from the Compton scatter equation to be:

$$\cos(\theta) = 1 - m_0 c^2 \left( \frac{1}{E_A} - \frac{1}{E_S + E_A} \right);$$ Eqn. 2 where $E_S$ and $E_A$ are the measured energies of the Compton recoil electron and Compton scattered photon in the scatter and absorption detectors, respectively. The uncertainties in $E_S$ and $E_A$ ($\Delta E_S$ and $\Delta E_A$) due to finite energy resolution of the detectors can be propagated through Eqn. 1 to determine the uncertainty in the calculated value of θ as follows:

$$\Delta\theta_E = \quad \text{Eqn. 3}$$
$$\frac{1}{\sin(\theta)}\left[\left(\frac{m_0c^2}{(E_S+E_A)}\Delta E_S\right)^2 + \left(\frac{m_0c^2}{E_A^2}\Delta E_A - \frac{m_0c^2}{(E_S+E_A)}\Delta E_A\right)^2\right]^{1/2};$$

which is equivalent to the following uncertainty:

$$\Delta\theta_E = \frac{m_0c^2}{E_0^2\sin(\theta)}\left[(\Delta E_S)^2 + \left(\frac{E_S(E_S+E_0)\Delta E_A}{E_A^2}\right)^2\right]^{1/2}. \quad \text{Eqn. 4}$$

The angular uncertainty due to detector spatial resolution and system geometry $\Delta\theta_{S/G}$ can be further divided into contributions from the scatter and absorption detectors, $\Delta\theta_S$ and $\Delta\theta_A$, respectively. It can generally be assumed that the planar resolution of each detector is square, that is, $\Delta x = \Delta y = \Delta xy$, as shown in FIG. 4. The angular uncertainties for a system using two parallel detectors are then given as:

$$\Delta\theta_S = \frac{1}{R_1^2}\left[\Delta xy_S^2(1+\alpha\cos\theta)^2 + (\Delta z_s\alpha\sin\theta)^2\right]^{1/2} \quad \text{Eqn. 5}$$

$$\Delta\theta_A = \frac{1}{R_2^2}\left[(\Delta xy_A\cos\theta)^2 + (\Delta z_A\sin\theta)^2\right]^{1/2};$$

$$R_2 = \frac{R_c}{\cos\theta}$$

$$\Delta\theta_{S/G} = [(\Delta\theta_S)^2 + (\Delta\theta_A)^2]^{1/2}$$

In addition, the total angular uncertainty of the system can be calculated from the energy resolution and spatial resolution/geometry uncertainties as follows:

$$\tan^2(\Delta\theta_{TOT}) = \tan^2(\Delta\theta_E) + \tan^2(\Delta\theta_{S/G}) \quad \text{Eqn. 6.}$$

Assuming that each detector event conical surface has the same angular uncertainty, the point where all cones intersect (the source point) will be approximately circular with a diameter of:

$$\Delta x = R_1 \tan \Delta\theta_{tot} \quad \text{Eqn. 7};$$

where $\Delta x$ is the position uncertainty of a point source at a distance $R_1$ from the scatter detector and is approximately equal to the spatial resolution of the image generated in this manner.

The radiation dose deposited in a subject can be calculated based on the energy of the photon scattered out of the subject, which is determined from energies deposited in the scatter and absorption detectors, and the angle $\theta_p$ at which the photon scattered in the subject. While the calculation of the angle and its implementation into a dose reconstruction algorithm is complex, the uncertainty of $\theta_p$ can be determined from other known parameters and calculated uncertainties. Rearrangement of the Compton scatter equation gives the initial linear accelerator (LINAC) photon energy as a function of the scattered photon energy and angle of scatter in the subject as follows:

$$(hv \pm \Delta hv) = \frac{(hv' \pm \Delta hv')}{1 - \frac{(hv' \pm hv')}{m_0c^2}[1-\cos(\theta_p \pm \Delta\theta_p)]}. \quad \text{Eqn. 8}$$

The uncertainty in the calculated initial photon energy $\Delta hv$ can be obtained by propagating the uncertainties of scattered photon energy $\Delta hv'$ and scattering angle $\Delta\theta_p$ through Eqn. 8. The scattered photon energy is equal to the sum of energies deposited in the scatter and absorption detectors of the Compton camera imager, and is therefore dependent on the energy resolutions of the two detectors, as given by:

$$(hv' \pm \Delta hv') = (E_S \pm \Delta E_S) + (E_A \pm \Delta E_A) \quad \text{Eqn. 9}$$
$$= (E_S + E_A) \pm \sqrt{(\Delta E_S)^2 + (\Delta E_A)^2};$$

and $$\Delta hv' = \sqrt{(\Delta E_S)^2 + (\Delta E_A)^2}. \quad \text{Eqn. 10}$$

Uncertainty associated with the scattering angle in the subject can be derived geometrically from the relationships illustrated in FIG. 4 from the fact that the sum of all angles in a triangle is 180 degrees and the angles of a line bisector sum to 180 degrees as follows:

$$\Delta\theta_p = |\theta_p - \theta_p'| = |\theta_p - \theta_p''|$$

$$\theta_p' + \Delta\theta_c + (180°-\theta_p) = 180° \to \theta_p' = \theta_p - \Delta\theta_c$$

$$(180°-\theta_p'') + \Delta\theta_c + \theta_p = 180° \to \theta_p'' = \theta_p + \Delta\theta_c$$

$$\Delta\theta_p = |\theta_p - \theta_p - \Delta\theta_c| = |\theta_p - \theta_p + \Delta\theta_c| = \Delta\theta_c \quad \text{Eqn. 11;}$$

where $\Delta\theta_c$ is equal to $\Delta\theta_{tot}$ of Eqn. 5 and the subscript c is added to distinguish Compton camera scattering angle from the subject scattering angle. Once the uncertainties for hv' and $\theta_p$ are calculated, they can be propagated through Eqn. 8 to determine the uncertainty in hv as follows:

$$\Delta hv = \left[\left(\frac{\partial hv}{\partial hv'}\Delta hv'\right)^2 + \left(\frac{\partial hv}{\partial \theta_p}\Delta\theta_p\right)^2\right]^{1/2} \quad \text{Eqn. 12}$$

$$\Delta hv = \left\{\left[\frac{\Delta hv'}{\left(1 - \frac{hv'}{m_0c^2}(1-\cos\theta_p)\right)^2}\right]^2 + \left[\frac{m_0c^2(hv')^2(\sin\theta_p)\Delta\theta_p}{(1-hv'(1-\cos\theta_p))^2}\right]^2\right\}^{1/2}.$$

Dose is determined by energy deposition in the subject and is therefore related to the energy of the Compton scattered electron, which can be obtained from the initial photon energy and the energy of the scattered photon, hv and hv', respectively. If binding energy of the electron is neglected, conservation of energy yields:

$$D = E_e = (hv \pm \Delta hv) - (hv' \pm \Delta hv')$$

$$\Delta D = \sqrt{(\Delta hv)^2 + (\Delta hv')^2} \quad \text{Eqn. 13.}$$

In this analysis, the energy of the Compton electron is referred to as the dose D. It should be noted that this is technically in accurate for two reasons. First, the energy transferred to the electron by the initial photon is actually defined as kerma rather than dose and; second, both dose and kerma are defined as energy deposited per unit mass. In essence, it is being assumed that charged particle equilibrium exists at the point of interaction and that all energy imparted to the electron is absorbed by the tissue at the point of interaction. Under these conditions, dose and kerma are equal.

Since the dosimetric uncertainty associated with a Compton scatter detector system is dependent on the angular uncertainty of the system, the models for angular uncertainty and dose uncertainty can be combined into a single algorithm in which all interdependencies are addressed. In this case, for each different Compton camera style, for example, parallel, ring, and stacked systems, there are a total of eleven variables that affect the spatial and dosimetric resolution of the system. These variables are: initial photon energy, distance between the source and the scatter detector, distance between scatter and absorption detectors, scatter detector element width/height and depth, scatter detector energy resolution, absorption detector width/height and depth, absorption detector energy resolution, photon scattering angle in the subject, and photon scattering angle in the scatter detector. This model can then be employed to determine the spatial resolution and dose accuracy provided by a CCI system having a selected set of parameters. For example, simulations show that a parallel detector system having the realistic system parameters $hv=2.0$ MeV, $\Delta xy_S=\Delta z_S=\Delta xy_A=\Delta z_A=1.0$ mm, $R_1=10.0$ cm, $R_2=20.0$ cm can provide a position resolution of less than 5 mm and a dose reconstruction better than 5 percent.

Though the above-discussed analytical modeling provides an estimation of system performance, it is generally directed to describing the uncertainties present in a given system and does not account for other variables affecting imaging performance. For example, the analytical model gives an analogue estimate of image resolution, but does not account for discretization of the volume of interest for display in image format. It also does not address the fact that image resolution can vary with direction depending on the type of Compton camera implemented. Therefore, the present invention also provides a non-deterministic system model for addressing such factors.

Generally speaking, iterative image reconstruction techniques are the most popular for CCI image reconstruction, but are also inherently slow for large image volumes (like those required for dose verification) and complicated imaging systems (like CCI's). As will be described, faster approaches, such as those based on filtered backprojection, are better suited to providing near real-time images for radiotherapy dose verification.

With the exemplary system described with respect to FIGS. 1a and 1b, the cone associated with each recorded CCI event can be back-projected into, for example, a 20-cm×20-cm×20-cm image space with isotropic 1-mm voxels using an accelerated threshold-based algorithm, such as will be described.

Turning specifically to reconstruction, generally, five numerical back-projection algorithms have been published to date; three of which are applicable to the parallel detector design illustrated in FIG. 3b. For example, the Source Space Tree Algorithm (SSTA) sorts through increasingly smaller image sub-volumes searching for volumes whose center is less than some threshold distance from the cone surface. If a sub-volume satisfies the threshold distance condition, it is further subdivided and the process continues until the individual voxels lying on the cone surface are identified; if not, the current sub-volume is discarded and the algorithm moves on. The Cone-Surface Mapping Algorithm (CSMA) proceeds in steps of size $\Delta R$ along the cone axis and radially samples the circular intersection of the cone surface with the plane perpendicular to the cone axis at each step, similar to the spokes on a wheel. A step size limit of one voxel in the horizontal or vertical direction ensures that enough radial samples are acquired to accurately identify all intersected voxels. Once complete, the cone coordinate system is translated back onto the global image coordinate system. While the SSTA and CSMA algorithms each require fewer than the $N^3$ (where N is the number of voxels along each side of the image volume) calculations needed for a direct cone surface intersection calculation, the accuracy of each is dependent on the threshold value (SSTA) or step size (CSMA) selected.

Wilderman et al., S. J. Wilderman, W. Les Rogers, G. F. Knoll and J. C. Engdahl, "Fast algorithm for list mode back-projection of Compton scatter camera data," IEEE Trans. Nucl. Sci. 45, 957-962 (1998), published a mesh-marching algorithm that has been shown to be more efficient than both the SSTA and CSMA methods. The algorithm essentially marches from one edge of the 2-dimensional image space to the other, finding the intersection of the cone and adjacent image space grid lines as necessary. This process is repeated for each slice of the image space for each CCI detector event. The marching algorithm does not depend on any thresholds or step sizes and is therefore always accurate, making it preferable to the previous algorithms for both accuracy and efficiency. This algorithm is considered to be the gold standard and serves as the basis of comparison for the new reconstruction algorithm presented in accordance with the present invention.

Figure 5:
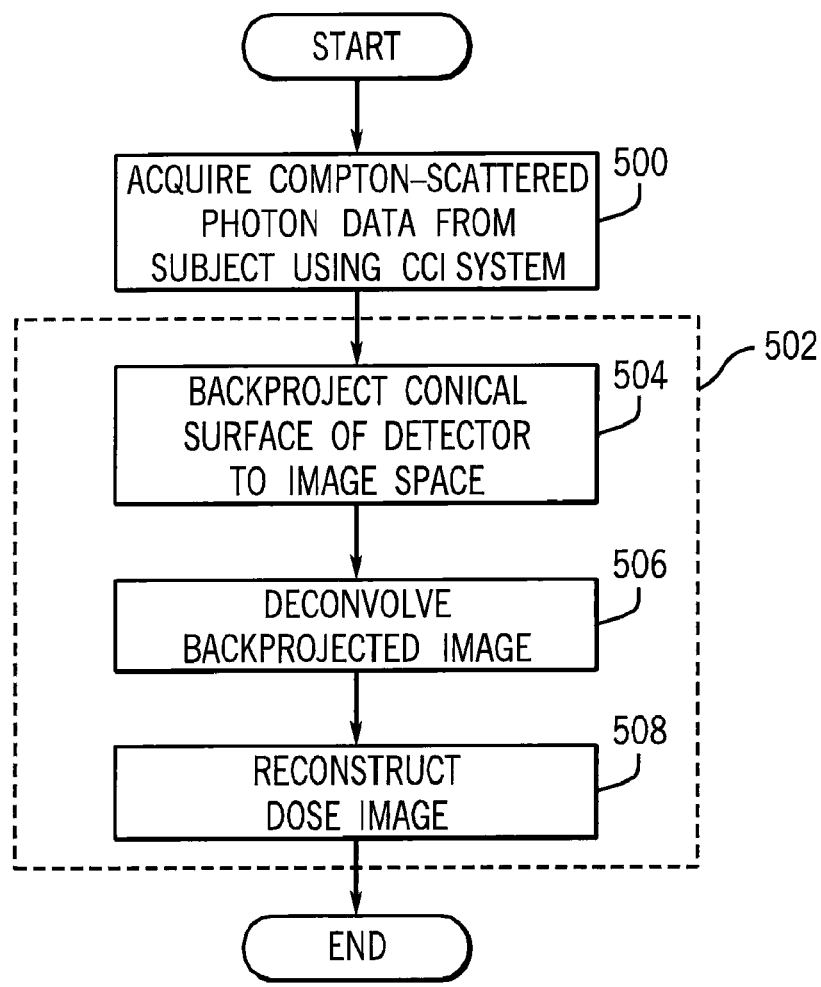
FIG. 5 is a flowchart setting forth the steps for creating an image for dose verification in accordance with the present invention.

Referring to FIG. 5, the present invention provides a method for reconstructing an image, that is a spatial representation, of dose delivered to a subject. As will be described, the present invention may utilize a threshold-based, back-projection algorithm. Specifically, the process begins at process block 500 by acquiring Compton-scattered photons from a subject of a radiotherapy procedure using a CCI system, such as described with respect to FIGS. 1a and 1b.

As generally indicated at 502, using the acquired Compton-scattered photon data provided by the CCI system, image reconstruction begins. In accordance with one aspect of the invention, a threshold-based, back-projection algorithm may be used as indicated at process block 504. Using the exemplary system configuration described above, the threshold-based, back-projection algorithm includes back-projecting the conical surface associated with each detector event into, for example, a 200×200×200-mm image space with isotropic 1-mm voxels.

Specifically, as discussed, the cone surface associated with a CCI detector event is described by three parameters: the apex, defined as the first detector interaction position $(x_1, y_1, z_1)$; the axis, defined as the normalized vector between the first and second interaction positions, $(n_x, n_y, n_z)$; and the half-angle $\theta$, defined as the Compton scattering angle at the first interaction position and calculated from conservation of energy and momentum for a photon collision with an electron. The intersection of this cone with the image volume is described as follows:

$$[n_x(x-x_1)+n_y(y-y_1)+n_z(z-z_1)]^2=(\cos\theta)^2[(x-x_1)^2+(y-y_1)^2+(z-z_1)^2]$$ Eqn. 14;

where $(x,y,z)$ are the spatial coordinates corresponding to a given image voxel. A solution matrix, S, can be obtained by subtracting the left side of Eqn. 14 from the right side, as follows:

$$S = |(\cos\theta)^2[(x-x_1)^2 + (y-y_1)^2 + (z-z_1)^2] - [n_x(x-x_1)+n_y(y-y_1)+n_z(z-z_1)^2]|.$$ Eqn. 15

The intersection of the cone with each plane (z) occurs at locations (x,y) where S is equal to zero and will be a full or partial ellipse. However, since the solution space is discretized, S will have very few (if any) zero-valued elements.

S is not a binary edge map, but rather a distance map representing the closeness of each voxel to the true elliptical intersection. A threshold function is used to extract the binary single-voxel-wide elliptical intersection from S.

A threshold function by which to extract a binary cone-plane intersection curve from the solution matrix was developed using observations that the optimum threshold value varies with distance from the cone apex (z) and with cone angle (θ). The dependence on z is a result of the changing relative definition of the cone-plane intersection within the solution matrix.

Figure 6A:
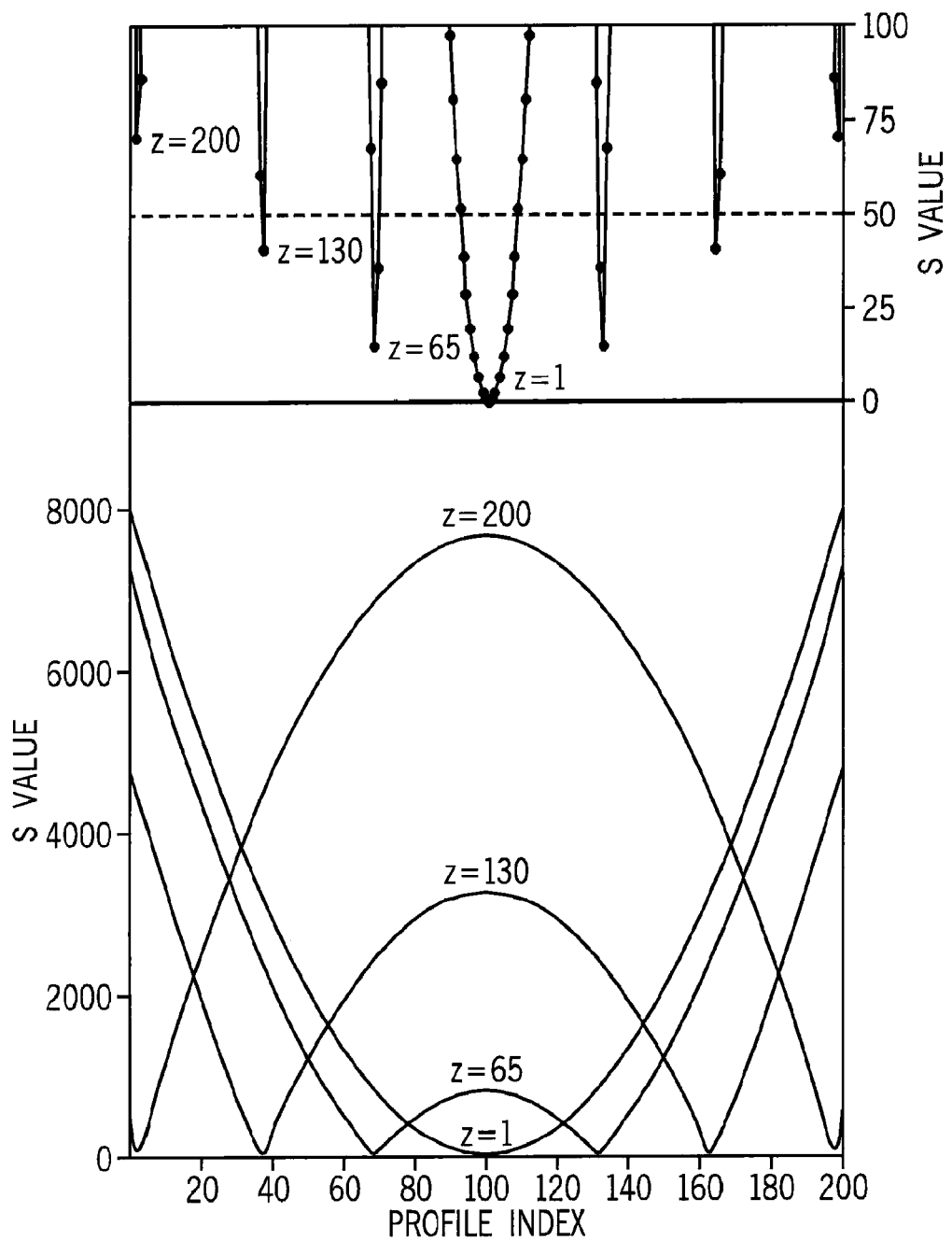
FIG. 6a is graph illustrating exemplary horizontal profiles of solution matrix, S, at various image planes for a cone surface showing a plurality of intersection points.
Figure 6B:
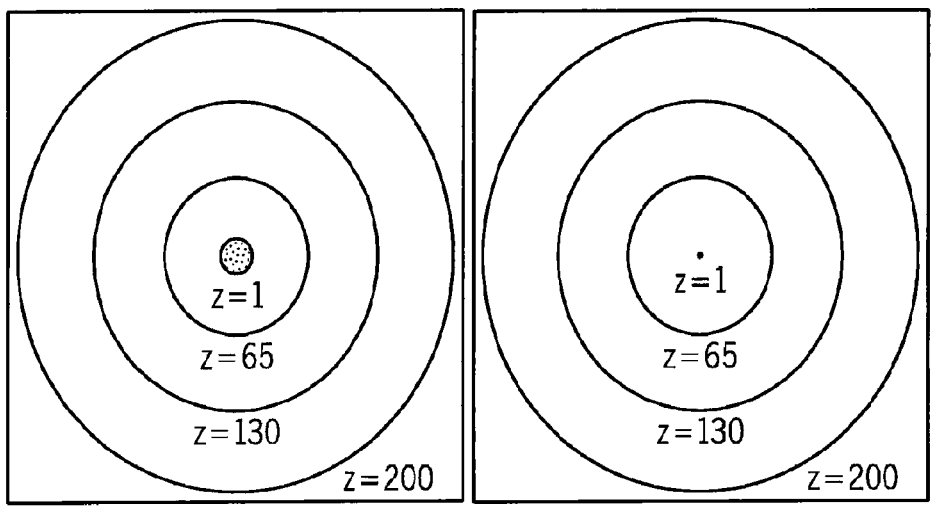
FIG. 6b is a graph illustrating exemplary results of thresholding all images slices in the solution matrix using a constant threshold (left) and a threshold function accounting for the distance between the cone apex and the image slice of interest (right)

Referring to FIG. 6a, horizontal profiles of S at various image planes for a cone with a half-angle of 26 degrees are shown. The image space used in these examples is 200 mm×200 mm×200 mm with isotropic 1-mm voxels. x, y, and z indices are accordingly reported in mm. In the plane containing the apex of the cone (z=1), the central S profile approximates a parabola with the minimum located at the true point of intersection. As z increases to represent those planes near the apex, the base of the parabola splits and widens to contain the two intersection points associated with the profile through the center of the (in this example) circular intersection, and an inverted parabola is formed in the region between these two points. As z continues to increase, the points of intersection continue to spread apart and the height of the inverted parabola between them increases. The valley around the intersection becomes narrower and the minima values increase. The result is a variation in the number of pixels with values close to that of the pixel nearest the true intersection. The inset in the upper portion of FIG. 5a illustrates the inaccuracy of a constant threshold value due to this variation. In this example, a threshold value of 50 (indicated by the dashed horizontal line) produces optimum results for z=130, but is too low for z=200 and too high for z=65 and z=1. The result of thresholding all image slices with T=50 is shown in FIG. 6b, where the extracted intersection curves for the planes mentioned above have been superimposed onto a single image. As expected, the algorithm performs well for z=130, but results in intersections that are either incomplete or too wide in other planes. As may be inferred from the curves in FIG. 6a, a threshold function that is linear in z, such as:

$$T = k \cdot z \quad \text{Eqn. 16;}$$

is effective in correcting for this effect, as illustrated in FIG. 6b. In Eqn. 16, k is an empirical constant, chosen for this example to be 0.5. It is noted that the nature of the threshold algorithm is such that an optimum constant, k, should be determined for a given system geometry (detector configuration and image space parameters).

Figure 6C:
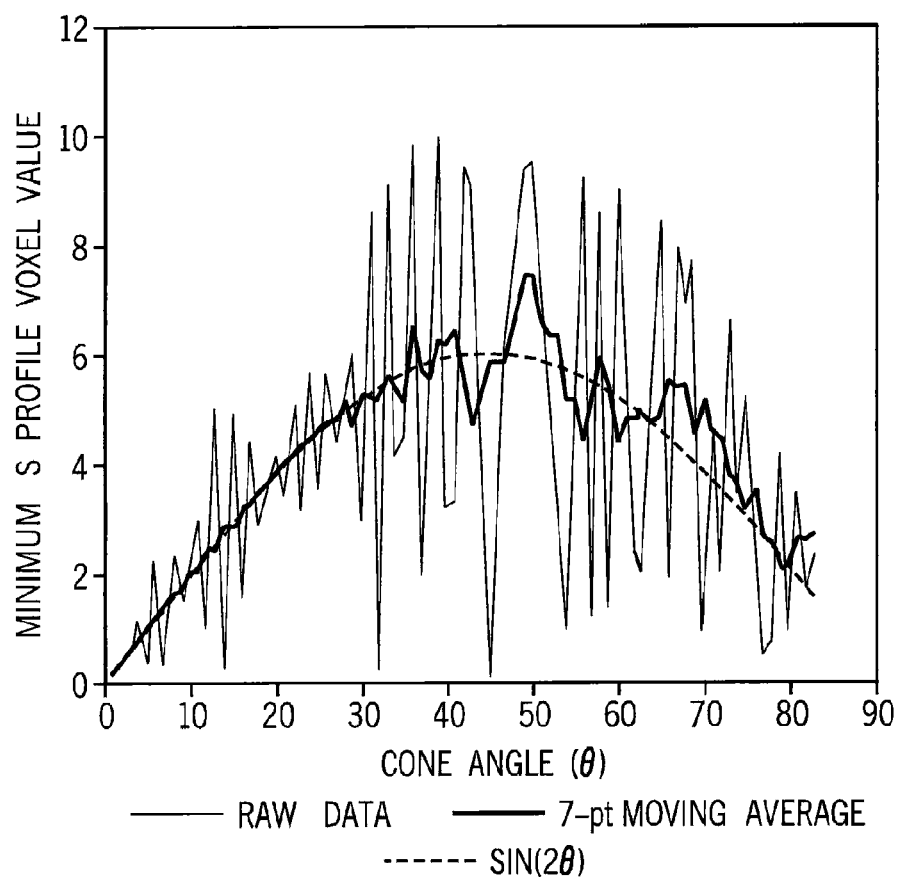
FIG. 6c is a graph illustrating the further dependence of an optimum threshold function on the angle of the backprojected cone.

A similar, but non-linear, behavior is observed as the half-angle of the cone (θ) increases, where the intersections extracted at the plane z=17 using Eqn. 16 for cone half-angles ranging from 8 degrees to 80 degrees. The calculated threshold is too high for small cone angles (extracted intersection is too wide), appropriate for mid-range angles, and again too high for large angles. This behavior suggests a sinusoidal threshold dependence on θ such that the threshold is lower for small and large cone angles and higher for intermediate angles. To confirm this observation, solution matrix profiles were examined as in the analysis of z-dependence. The same slice was extracted from the solution matrix for each cone having a half-angle in the range of 1 degree to 83 degrees. The minimum of the central horizontal profile was then extracted and plotted as a function of cone angle. This minimum value corresponds to the value of the pixel nearest the true cone-plane intersection along the profile line. The results are plotted in FIG. 6c. Though noisy, a sin(2θ) trend is readily observed. The threshold equation can then updated to correct for the effects of cone angle dependence as follows:

$$T = k \cdot z \cdot |\sin(2\theta)| \quad \text{Eqn. 17.}$$

The implementation of the threshold in Eqn. 16 effectively extracts single-pixel-wide cone-plane intersections from the solution matrix at all values of z over a wide range of cone angles. There is an additional dependence on the angle of the cone axis with the image plane, but this effect is generally minimal.

Referring again to FIG. 5, following the backprojection of the surface of the detector to image space at process block 504, the back-projected image is deconvolved at process block 506. The deconvolution is performed using a pseudo-inverse deconvolution algorithm and a simulated point spread function (PSF). The PSF includes a back-projected image of a monoenergetic point photon source located at the center of the image volume. Thereby, an image of energy dose delivered to the subject is created at process block 508. In the reconstructed image, the intensity of each voxel is proportional to the source intensity at the corresponding physical location in the subject, and therefore to the number of source photon interactions at that position.

Simulated Comparisons

The threshold algorithm of the present invention can be implemented in the matrix-based computing language, such as MATLAB, which is commercially available from The MathWorks Inc., of Natick, Mass., which is fundamental to the speed of the algorithm. MATLAB is optimized for matrix calculations and allows the solution matrix, S, to be solved for each image plane (or the entire image volume) in a single step, rather than looping through each voxel position (x,y,z). Equation 14 can be vectorized using the meshgrid function included in the MATLAB function library. This function takes as input two vectors containing voxel x- and y-coordinates, respectively, and returns two matrices (X and Y) where the rows of X are replications of the x-vector and the columns of Y are replications of the y-vector. The use of the meshgrid function reduces the calculation of the solution matrix to a single computation in MATLAB as follows:

$$S = (\cos \alpha)^2 [(X-x_1)^2 + (Y-y_1)^2 + (z-z_1)^2] - [n_x(X-x_1) + n_y(Y-y_1) + n_z(z-z_1)]^2 \quad \text{Eqn. 18.}$$

The algorithm begins by extracting the detector interaction positions and energies from the CCI event data set, then calculates the cone axis and angle. For each detector event, the program loops through the planes of the image volume, solving Eqn. 15 for increasingly larger values of z. It is possible to obtain all three dimensions of S using a single calculation by including z in the meshgrid operation; however, the looping approach is less complicated given the dependence of the threshold function on z and no significant computational advantage is observed when a three-dimensional calculation is implemented.

The marching algorithm described above can also be implemented using MATLAB and optimized for the best possible runtimes. The algorithm can be written as described by Wilderman et al., and proceeds for each image slice associated with a given detector event.

As with the threshold algorithm of the present invention, the marching algorithm can be vectorized wherever possible, including the subroutine that calculates the intersection of the cone with each grid line as the algorithm proceeds. Each call to the subroutine generates at most two points of intersection, the associated pixels of which are tagged simultaneously. This reduces the maximum number of steps from 2N in the published algorithm to N. It should be noted that the structure of the marching algorithm does not lend itself well to vectorization in general, and hence the properties of MATLAB that make it well suited to the threshold algorithm also make it somewhat ill-suited to the marching algorithm. In other words, the marching algorithm represents the fastest possible implementation in MATLAB, but not necessarily the fastest global implementation.

A Monte Carlo model of a parallel planar CCI system similar to that shown in FIG. 3a was created using MCNPX and a point isotropic photon source simulated at a distance of 10 cm from the center of the scatter detector. The model was ideal in that both scatter and absorption detectors were designed with essentially infinite spatial and energy resolutions, and multiple scatter events in the scatter detector were discarded. The scatter and absorption detectors were modeled as parallel 20-cm×20-cm planes positioned 5 cm apart. Interaction positions and energies were extracted from the MCNPX PTRAC output file to generate a list of distilled detector event data that could be utilized by both the threshold and marching algorithms described above. Data sets consisting of $10^4$ detector events were simulated and back-projected using both methods into a 20 cm×20 cm×20 cm image space with isotropic 1-mm voxels. In order to quantify any differences that may exist and thereby evaluate the performance of the threshold algorithm, a number of statistical parameters were calculated for each three-dimensional image. The maximum value of each image was calculated as an indicator of algorithm accuracy. Since $10^4$ detector events were back-projected and each should intersect the true point source location only once, the maximum image intensity is expected to be $10^4$ and should occur only at the image voxel corresponding to the physical location of the simulated point source. The minimum, mean, standard deviation, and sum values are also indicative of accuracy and efficiently highlight any deficits of the threshold algorithm when compared to the gold-standard marching algorithm. By design, the marching algorithm generates a complete single-pixel-wide curve for each cone-plane intersection, while the threshold algorithm is dependent on the selection of an optimum threshold function to generate such curves. A perfect function cannot be attained, and therefore the image generated by the threshold algorithm will always differ to some degree from the marching algorithm image. These differences were used to determine an optimum value of k in Eqn. 17.

Back-projected image quality of the threshold algorithm relative to the marching algorithm was tested using the signal-to-noise ratio (SNR, defined here as the ratio between the maximum voxel intensity and the mean value of all other voxels) and the full-width-at-half-maximum (FWHM) of the image along all three axes. Ideally, the SNR and FWHM values of the images would be identical, indicating that the threshold algorithm extracts exact cone-plane intersections in all situations.

When compared to the current state-of-the art marching algorithm developed by Wilderman et al., the threshold algorithm of the present invention performed well. The expected differences in the reconstructed images due to imperfect thresholding were on the order of a few percent and were offset by a 75 percent reduction in computation time. Improved accuracy may be obtained by accounting for threshold dependence on the angle between the detector (or image) plane and the cone axis, a step which may be necessary for CCI detector configurations that encourage large detector scattering angles. Such a correction, however, would be detrimental to computation time as this angle is not currently necessary for back-projection of the detector data and is therefore not computed. Analysis of the results obtained here using a parallel detector configuration indicate that implementation of the correction would provide limited improvement and, in some cases, may not be worth the computational cost.

The nature of the threshold algorithm is such that an optimum constant, k, should be determined for a given system geometry (detector configuration and image space parameters). The constant deemed to be optimum for the system described here will not be so for a different system. For example, decreasing the voxel dimensions of the image space in the current study could potentially increase the number of voxels in the solution matrix having values below the calculated threshold, resulting in increased width of the extracted cone-plane intersection curves. As with the cone axis angle, a correction factor could be implemented in Eqn. 16 to address such modifications, but is not necessary at present.

In summary, the approximate back-projection algorithm for Compton camera data in accordance with the present invention provides a faster alternative to the current back-projection methods at a limited expense of exactitude in cone surface reconstruction. The cost is greatest at the edges of the image volume, and can be globally minimized via careful determination of a threshold function appropriate to the CCI system in use. This algorithm is well-suited to situations involving the acquisition of a large number of high-resolution (or large field of view) images, where the initial time investment required to develop an optimum threshold function is more than offset by the decreased image back-projection time.

Again, the accelerated threshold-based algorithm generates a binary 3D image of each conical surface and sums the individual images together to produce a back-projected image. This image is then deconvolved using a simulated point spread function (PSF) and the Wiener deconvolution algorithm. The PSF consisted of a back-projected image of a monoenergetic point photon source located at the center of the image volume. Both the back-projected image and the PSF were normalized prior to filtering to account for large differences in intensities between the two. Due to the asymmetric nature of the back-projected images in the direction perpendicular to the detector surface mentioned earlier, a windowing function may be applied to the back-projected image to prevent artifacts associated with high gradient transitions in frequency domain deconvolution. In this instance, a tapered cosine window (alpha=0.6) is often desirable, but experience indicates that this choice may not be appropriate in all circumstances, as the window function employed can have a significant impact on reconstructed image quality. For this model, the tapered cosine window produces more accurate results relative to the known energy deposition.

Using the above-described algorithm, the relative intensities of the reconstructed images were found to be very similar to those of images created from tallied energy deposition values under a variety of clinical conditions, with the exception that an incident photon beam having a bremsstrahlung energy spectrum (6 MV) produced images of decreased relative intensity as a result of photoelectric contributions to energy deposition. A correction factor based on the photoelectric cross-section can be applied for some clinical implementations. The dose reconstruction and verification technique based on the detection of scattered photons from the patient using a Compton camera imaging system is clinically viable.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:

1. A method for determining a dose of radiation delivered to a subject receiving radiotherapy, the method comprising the steps of:
   a) acquiring photons resulting from Compton scatter in the subject using a Compton camera imager to produce a set of acquired Compton photon data;
   b) backprojecting the acquired Compton photon data from the Compton camera imager to image space;
   c) deconvolving the backprojected Compton photon data; and
   d) reconstructing an image of the dose delivered to the subject from the deconvolved, backprojected Compton photon data.

2. The method of claim 1 wherein, in the image of the dose delivered to the subject, an intensity of each voxel is proportional to a number of source photon interactions at a corresponding location in the subject.

3. The method of claim 1 wherein step b) backprojecting the acquired Compton photon data from a cone surface associated with the Compton camera to an image volume.

4. The method of claim 3 wherein the cone surface associated the Compton camera is defined by an apex, defined with respect to a first detector interaction position $(x_1,y_1,z_1)$; an axis, defined as a normalized vector between the first interaction position and a second interaction position, $(n_x,n_y,n_z)$; and a half-angle $\theta$, defined as a Compton scattering angle at the first interaction position and calculated from conservation of energy and momentum for a photon collision with an electron.

5. The method of claim 4 wherein an intersection of the cone surface with the image volume is described by:

$$[n_x(x-x_1)+n_y(y-y_1)+n_z(z-z_1)]^2=(\cos\theta)^2[(x-x_1)^2+(y-y_1)^2+(z-z_1)^2];$$

where (x,y,z) are the spatial coordinates corresponding to a given image voxel.

6. The method of claim 5 wherein a solution matrix, S, is defined by:

$$S = |(\cos\theta)^2[(x-x_1)^2 + (y-y_1)^2 + (z-z_1)^2] - [n_x(x-x_1) + n_y(y-y_1) + n_z(z-z_1)]^2|;$$

and
   wherein step b) includes applying a threshold function to extract a binary, single-voxel-wide elliptical intersection from the solution matrix.

7. The method of claim 1 wherein step c) includes performing at least one of a pseudo-inverse deconvolution algorithm and a simulated point spread function (PSF).

8. The method of claim 7 wherein the PSF includes a back-projected image of a monoenergetic point photon source located at a center of an image volume associated with the subject.

9. The method of claim 1 wherein step a) includes acquiring photons resulting from Compton scatter in the subject using a first Compton camera imager configured to receive a first set of Compton photon data corresponding to Compton scatter in the subject at least due to the radiotherapy process and a second Compton camera imager configured to receive a second set of Compton photon data corresponding to Compton scatter in the subject at least due to the radiotherapy process.

10. The method of claim 9 wherein the first and second Compton camera imager extend along respective planes proximate to the subject.

11. The system of claim 10 wherein the first and second Compton camera imager extend along respective planes that are at least one of substantially perpendicular and substantially parallel.

12. The system of claim 11 wherein the respective planes share an adjacent axis extending along an intersection of the respective planes.

13. The system of claim 12 wherein the first and second Compton camera imager extend along respective planes proximate to the subject.

14. The system of claim 12 wherein the first and second Compton camera imager include at least one of a scatter detector and an absorption detector.

15. The system of claim 14 wherein deconvolving the backprojected Compton photon data includes performing at least one of a pseudo-inverse deconvolution algorithm and a simulated point spread function (PSF).

16. The system of claim 14 wherein backprojecting includes backprojecting the acquired Compton photon data from a cone surface associated with each of the first and second Compton camera to an image volume.

17. The system of claim 12 wherein the processor is configured to backproject the first and second sets of Compton photon data, deconvolve the backprojected Compton photon data, and reconstruct an image of the dose delivered to the subject from the deconvolved, backprojected Compton photon data to o reconstruct an image of a dose delivered to the subject using the first and second set of Compton photon data.

18. The system of claim 9 wherein the first and second Compton camera imager include at least one of a scatter detector and an absorption detector.

19. The system of claim 18 wherein the first and second Compton camera imager extend along respective planes that are substantially parallel.

20. The system of claim 19 wherein the scatter detector is arranged proximate to the subject and the absorption detector is arranged proximate to the scatter detector and away from the subject.

21. A system for performing a radiotherapy process comprising:
   a patient support configured to receive a subject of a radiotherapy process;
   a radiation source configured to deliver radiation to the subject in accordance with the radiotherapy process;
   a first Compton camera imager configured to receive a first set of Compton photon data corresponding to Compton scatter in the subject at least due to the radiotherapy process;
   a second Compton camera imager configured to receive a second set of Compton photon data corresponding to Compton scatter in the subject at least due to the radiotherapy process; and
   a processor connected to receive at least the first and second set of Compton photon data and configured to reconstruct an image of a dose delivered to the subject using the first and second set of Compton photon data, wherein an intensity of each voxel in the image of the dose delivered to the subject is substantially proportional to a number of source photon interactions at a corresponding location in the subject during the radiotherapy process.

22. The system of claim 21 wherein the first and second Compton camera imager extend along respective planes that are substantially perpendicular and share an adjacent axis extending along an intersection of the respective planes that are substantially perpendicular.

* * * * *

UNITED STATES PATENT AND TRADEMARK OFFICE
CERTIFICATE OF CORRECTION

PATENT NO. : 8,515,011 B2
APPLICATION NO. : 13/375568
DATED : August 20, 2013
INVENTOR(S) : Daniel W. Mundy et al.

It is certified that error appears in the above-identified patent and that said Letters Patent is hereby corrected as shown below:

Please delete the Title Page and replace with the attached Title Page.

In the Specifications

Column 7, Line 62, Eqn. 8:

" $$(h\nu \pm \Delta h\nu) = \frac{(h\nu' \pm \Delta h\nu')}{1 - \frac{(h\nu' \pm h\nu')}{m_0 c^2}\left[1 - \cos(\theta_p \pm \Delta\theta_p)\right]}$$ "

should be

-- $$(h\nu \pm \Delta h\nu) = \frac{(h\nu' \pm \Delta h\nu')}{1 - \frac{(h\nu' \pm \Delta h\nu')}{m_0 c^2}\left[1 - \cos(\theta_p \pm \Delta\theta_p)\right]}$$ --.

In the Claims

Column 16, Lines 18-64, Claims 16-22 should be removed, as only 1-15 were allowed.

Signed and Sealed this
Eleventh Day of February, 2014

Michelle K. Lee
*Deputy Director of the United States Patent and Trademark Office*

(12) United States Patent
Mundy et al.

(10) Patent No.: US 8,515,011 B2
(45) Date of Patent: Aug. 20, 2013

(54) SYSTEM AND METHOD FOR DOSE VERIFICATION RADIOTHERAPY

(75) Inventors: Daniel W. Mundy, Rochester, MN (US); Michael G. Herman, Rochester, MN (US)

(73) Assignee: MAYO Foundation for Medical Education and Research, Rochester, MN (US)

(*) Notice: Subject to any disclaimer, the term of this patent is extended or adjusted under 35 U.S.C. 154(b) by 9 days.

(21) Appl. No.: 13/375,568

(22) PCT Filed: Jun. 2, 2010

(86) PCT No.: PCT/US2010/037067
§ 371 (c)(1),
(2), (4) Date: Feb. 24, 2012

(87) PCT Pub. No.: WO2010/141583
PCT Pub. Date: Dec. 9, 2010

(65) Prior Publication Data
US 2012/0140887 A1 Jun. 7, 2012

Related U.S. Application Data

(60) Provisional application No. 61/183,146, filed on Jun. 2, 2009.

(51) Int. Cl.
*A61N 5/10* (2006.01)
*G01N 23/201* (2006.01)

(52) U.S. Cl.
USPC .................. 378/65; 378/70; 378/86

(58) Field of Classification Search
USPC .......................... 378/6, 65, 70, 86
See application file for complete search history.

(56) References Cited

U.S. PATENT DOCUMENTS

| | | | | |
|---|---|---|---|---|
| 5,270,925 A | * | 12/1993 | Stegehuis | 378/7 |
| 5,317,616 A | * | 5/1994 | Swerdloff et al. | 378/65 |
| 5,528,650 A | * | 6/1996 | Swerdloff et al. | 378/65 |
| 5,696,806 A | * | 12/1997 | Grodzins et al. | 378/86 |
| 5,903,008 A | * | 5/1999 | Li | 250/363.04 |
| 5,905,809 A | * | 5/1999 | Timmer | 382/131 |
| 6,714,620 B2 | * | 3/2004 | Caflisch et al. | 378/65 |
| 7,471,813 B2 | * | 12/2008 | Ulmer et al. | 382/128 |
| 7,496,171 B2 | * | 2/2009 | Rinkel et al. | 378/7 |
| 7,573,039 B2 | * | 8/2009 | Smith | 250/370.09 |
| 7,623,625 B2 | * | 11/2009 | Boyden et al. | 378/86 |
| 8,107,589 B2 | * | 1/2012 | Sakurai et al. | 378/65 |
| 2002/0044628 A1 | | 4/2002 | Hussein et al. | |
| 2004/0017889 A1 | | 1/2004 | Kumakhov | |
| 2005/0023474 A1 | | 2/2005 | Persyk et al. | |
| 2006/0138332 A1 | | 6/2006 | Bryman | |
| 2008/0224061 A1 | | 9/2008 | Smith | |

OTHER PUBLICATIONS

International Search Report and Written Opinion under date of mailing of Jan. 14, 2010 in connection with PCT/US2010/037067.

* cited by examiner

*Primary Examiner* — Alexander H Taningco
(74) *Attorney, Agent, or Firm* — Quarles & Brady, LLP

(57) ABSTRACT

A system and method for performing dose verification during radiation therapy. The system images photons created by Compton scatter events in the patient receiving treatment using a Compton camera imager (CCI). A dose reconstruction method is provided to reconstruct acquired Compton scatter photon data to produce an image showing dose deposition in the subject.

15 Claims, 7 Drawing Sheets

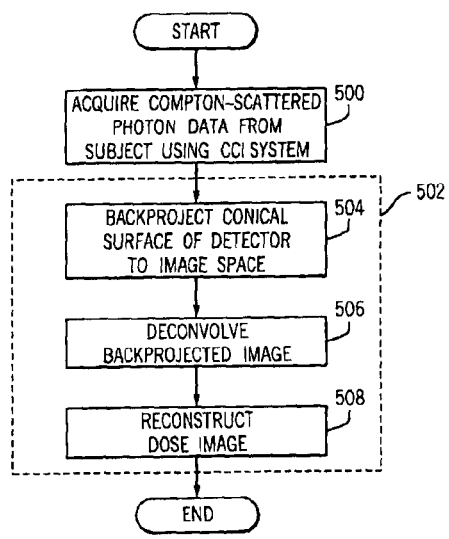

UNITED STATES PATENT AND TRADEMARK OFFICE
CERTIFICATE OF CORRECTION

PATENT NO.        : 8,515,011 B2  
APPLICATION NO.   : 13/375568  
DATED             : August 20, 2013  
INVENTOR(S)       : Mundy et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 90 days.

Signed and Sealed this

Fifteenth Day of September, 2015

Michelle K. Lee
*Director of the United States Patent and Trademark Office*